(12) United States Patent
Deshmukh et al.

(10) Patent No.: US 9,932,295 B2
(45) Date of Patent: Apr. 3, 2018

(54) PROCESS FOR PREPARATION OF LEVOTHYROXINE AND SALTS THEREOF

(71) Applicant: LUPIN LIMITED, Mumbai (IN)

(72) Inventors: Swapnil Sudhakar Deshmukh, Maharashtra (IN); Adinath Murlidhar Jain, Maharashtra (IN); Himanshu Madhav Godbole, Maharashtra (IN); Girij Pal Singh, Maharashtra (IN); Dinesh Dnyaneshwar Dixit, Maharashtra (IN)

(73) Assignee: LUPIN LIMITED, Mumbai (IN)

( * ) Notice: Subject to any disclaimer, the term of this patent is extended or adjusted under 35 U.S.C. 154(b) by 0 days.

(21) Appl. No.: 15/300,145

(22) PCT Filed: Mar. 30, 2015

(86) PCT No.: PCT/IB2015/052330
§ 371 (c)(1),
(2) Date: Sep. 28, 2016

(87) PCT Pub. No.: WO2015/151013
PCT Pub. Date: Oct. 8, 2015

(65) Prior Publication Data
US 2017/0183292 A1 Jun. 29, 2017

(30) Foreign Application Priority Data

Mar. 31, 2014 (IN) .......................... 1233/MUM/2014

(51) Int. Cl.
*C07C 227/00* (2006.01)
*C07C 227/16* (2006.01)

(52) U.S. Cl.
CPC .................................. *C07C 227/16* (2013.01)

(58) Field of Classification Search
None
See application file for complete search history.

(56) References Cited

U.S. PATENT DOCUMENTS

| 2,579,668 A | 12/1951 | Hems et al. |
| 2,886,592 A | 5/1959 | Hillman |
| 4,997,946 A | 3/1991 | Edgar et al. |
| 2012/0296113 A1 | 11/2012 | Viscardi et al. |

FOREIGN PATENT DOCUMENTS

| IT | MI981997 | 3/2000 |
| WO | 2009136249 | 11/2009 |
| WO | 2015011573 | 1/2015 |

OTHER PUBLICATIONS

Chalmers et al. J. Chem. Soc., 1949; 3424-33.*

* cited by examiner

*Primary Examiner* — Sudhakar Katakam
*Assistant Examiner* — Ana Z Muresan
(74) *Attorney, Agent, or Firm* — Duane Morris LLP; J. Rodman Steele, Jr.; Gregory M. Lefkowitz

(57) ABSTRACT

The present invention relates to a process for the preparation of Levothyroxine and salts thereof. The process described in the present invention provides increase in the yields and purity comprising the use of sodium iodide and sodium hypochlorite as iodinating agent.

10 Claims, No Drawings

PROCESS FOR PREPARATION OF LEVOTHYROXINE AND SALTS THEREOF

FIELD OF THE INVENTION

The present invention relates to a process for the preparation of Levothyroxine and salts thereof.

BACKGROUND OF THE INVENTION

Levothyroxine, also L-thyroxine or $T_4$, is a synthetic form of the thyroid hormone thyroxine, which is normally secreted by the follicular cells of the thyroid gland. Thyroid hormone increases the metabolic rate of cells of all tissues in the body. In the fetus and newborn, thyroid hormone is important for the growth and development of all tissues including bones and the brain. In adults, thyroid hormone helps to maintain brain function, utilization of food, and body temperature, among other effects.

Levothyroxine Sodium contain synthetic crystalline L-3, 3',5,5'-tetraiodothyronine sodium salt [Levothyroxine (T4) sodium]. O-(4-hydroxy-3,5-diiodo-phenyl)-3,5-diiodo-1-tyrosine sodium i.e., Levothyroxine sodium has the following chemical structure

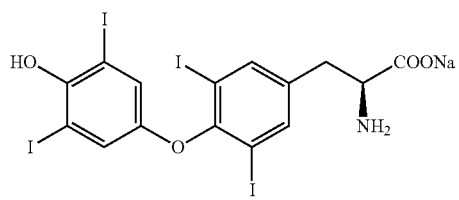

(I)

Levothyroxine sodium is approved to treat hypothyroidism to suppress thyroid hormone release from cancerous thyroid nodules, and to prevent growth of goiters. In addition, it is also used to treat conditions such as myoedema, cretinism and obesity.

*J Chem. Soc*, (1949); 3424-33 describes a process for the synthesis of mono sodium salt of Levothyroxine comprising the steps of: (a) nitration of Levo tyrosine; (b) protection of the amino group; c) protection of the carboxy group; (d) oxidative coupling; (e) hydrogenation of the nitro groups to amino groups; (f) diazotization followed by iodination; (g) demethylation of the Me ether and hydrolysis; (h) which on iodination in presence of iodine to obtain Levothyroxine, which is further converted in to Levothyroxine sodium.

IT 1302201 disclosed a process for the synthesis of mono sodium salt of Levothyroxine with an improved overall yield compared to a similar process disclosed in *J Chem. Soc*, (1949) 3424-33. IT 1302201 discloses a process for preparing Levothyroxine comprising reacting 3,5 diiodo-L-thyronine with iodine and potassium iodide.

*Journal of the Chemical Society*, 840-3; 1950, discloses a process for the preparation of Levothyroxine comprising reacting 3,5 diiodo L-thyronine with $KI_3$ in water and ethylamine.

U.S. Pat. No. 2,579,668 discloses a process for the preparation of Levothyroxine comprising reacting 3,5 diiodo-L-thyronine with iodine in a solvent selected from water, dioxane, lower aliphatic alcohols and mixtures thereof, in the presence of an organic base selected from the group consisting of piperidine, morpholine and amines.

U.S. Pat. No. 2,886,592 discloses a process for the preparation of Levothyroxine comprising reacting 3,5 diiodo-L-thyronine with N-iodoacetamide in absolute methanol in presence of triethylamine.

*Vestsi Natsyyanal'nai Akademii Navuk Belarusi, Seryya Khimichnykh Navuk*, (1), 85-92; 2004 discloses a process for the preparation of Levothyroxine comprising reacting 3,5 diiodo L-thyronine with iodine & potassium iodide in water & methanol in presence of ammonia.

WO 2009136249 discloses a process for the preparation of Levothyroxine comprising reacting 3,5-diiodo-4-p-hydroxy phenoxy-L-phenyl alanine hydrochloride with methyl amine and Iodine source such as iodine and/or potassium iodide.

US 20120296113 discloses a process for the synthesis of mono sodium salt of Levothyroxine comprising reacting 3,5 diiodo-L-thyronine with an iodinating agent such as NaI & $I_2$, in the presence of an aliphatic amine.

These above mentioned processes have number of disadvantages such as (a) use of highly expensive iodinating agent like iodine, potassium iodide, $KI_3$, N-iodoacetamide and sodium iodide.

(b) the use of high amount of iodinating agent such as iodine, potassium iodide, $KI_3$, N-iodoacetamide and sodium iodide for iodination is not recommendable at commercial scale, (c) yield of above reactions is very less that makes the process less effective from an economic point of view.

In view of problems in commercialization of process for the preparation of Levothyroxine and its salts, there is a need for simple, cost effective, commercially feasible, industrially scalable and environmentally friendly process for the preparation of Levothyroxine and its salts with high purity and yield.

The iodinating agent plays a crucial role in multi-step synthesis of organic molecule like Levothyroxine having variety of functional groups. Surprisingly, it has been found that if sodium iodide & sodium hypochlorite is used in the desired iodination step, the yield of iodination reaction is good. Another advantages is both sodium iodide & sodium hypochlorite are cheaper than any other iodinating agent which results in significant cost savings compared to the other known process.

The object of the present invention is to provide an industrially advantageous process for the preparation of Levothyroxine and its salts with overall high yield and purity.

SUMMARY OF THE INVENTION

The present invention relates to a process for the preparation of Levothyroxine of formula (II)

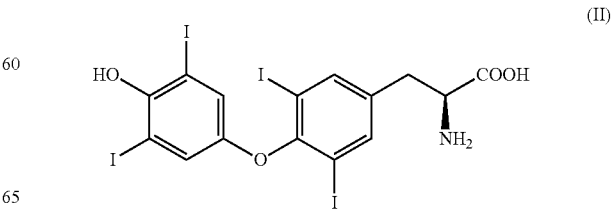

(II)

comprising iodination of compound of formula (III)

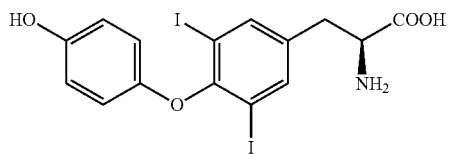

with sodium iodide and sodium hypochlorite in the presence of an aliphatic amine.

The present invention also relates to a process for the preparation of Levothyroxine sodium of formula (I)

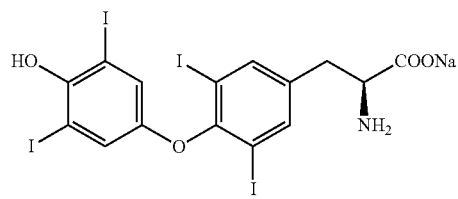

comprising the steps of (a) iodination of compound of formula (III) with sodium iodide and sodium hypochlorite in the presence of an aliphatic amine to obtain Levothyroxine of formula (II)

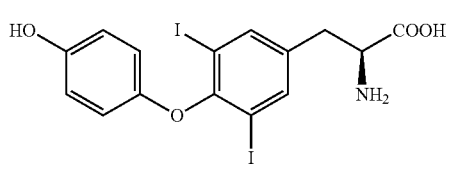

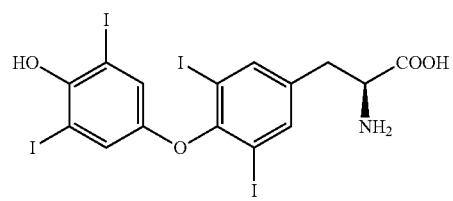

(b) treating Levothyroxine of formula (II) with sodium hydroxide to obtain Levothyroxine disodium of formula (IV)

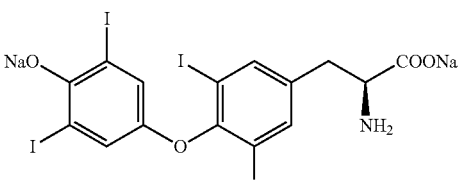

(c) converting Levothyroxine disodium of formula (IV) to Levothyroxine sodium of formula (I).

DETAILED DESCRIPTION OF THE INVENTION

The inventors have found that unlike U.S. Pat. No. 2,579,668 discussed above, which discloses a process for the preparation of Levothyroxine comprising reacting 3,5 diiodothyronine with iodine in the presence of organic base in a suitable solvent from which the yield is varies from 47-90%, the process of the present invention has higher yield. The process described for iodination in the present invention always employed the yield of Levothyroxine more than 92%.

The present invention relates to a process for the preparation of Levothyroxine of formula (II)

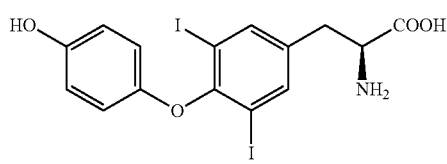

comprising iodination of compound of formula (III) with sodium iodide and sodium hypochlorite in the presence of an aliphatic amine The iodination reaction is carried out in the presence of an aliphatic amine. The aliphatic amine is selected from the group consisting of methyl amine, ethyl amine, propyl amine, isopropyl amine, tert-butyl amine, diisopropyl amine, diisopropyl ethyl amine, n-hexyl amine, morpholine and triethylamine or mixtures thereof. In a preferred embodiment said aliphatic amine is selected from methyl amine, tert-butyl amine, diisopropyl amine and morpholine.

The iodination reaction is carried out in a suitable solvent. As suitable solvent, water, dioxane, lower aliphatic alcohols such as methanol or ethanol or mixtures thereof may be used. In a preferred embodiment, iodination reaction is carried out in a water or methanol or mixtures thereof.

Iodination reaction is conveniently carried out at a temperature of from 0° C. to 40° C., preferably at 20° C. to 30° C. The Levothyroxine of formula (II) was isolating by methods known in the art.

In one embodiment, present process further comprising reacting Levothyroxine of formula (II) with sodium source such as sodium carbonate or sodium bicarbonate to obtain Levothyroxine sodium of formula (I)

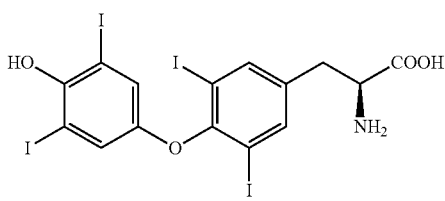

(II)

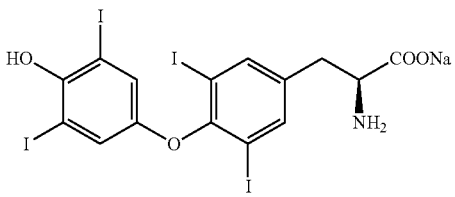

(I)

This step is carried out optionally in a solvent. A suitable solvent is selected from the group consisting of water, alcohols, amides, sulphoxides, ethers, hydrocarbons, halogenated hydrocarbons, ketones, esters and nitriles or mixtures thereof. Examples of suitable solvent includes, but are not limited to water, methanol, ethanol, n-propanol, isopropanol, butanol, iso-butanol, ethyl acetate, methyl acetate, tertiary butyl acetate, isopropyl acetate, acetone, methyl isobutyl ketone, methyl ethyl ketone, diethyl ketone, dimethyl ketone, methyl isobutyl ketone, toluene, ethyl ether, methyl ether, diisopropylether, methyltertbutylether, dioxane, tetrahydrofuran, N,N-dimethylformamide, N-methyl acetamide, N,N-dimethylacetamide, dimethylsulfoxide, 1,1-dichloroethane, dichloromethane, chloroform, acetonitrile, benzene, xylene or mixtures thereof. This step is carried out at a temperature of from 40° C. to 100° C., preferably at 80° C. to 90° C.

In a preferred embodiment, this step is carried out by reacting Levothyroxine of formula (II) with aqueous sodium carbonate in n-propanol and isolating the compound of formula (I) by methods known in the art.

The present invention also relates to a process for the preparation of Levothyroxine sodium of formula (I)

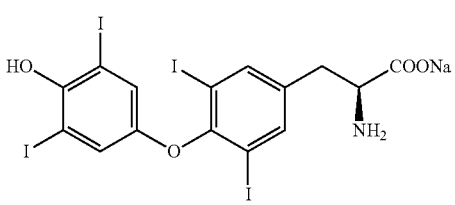

(I)

comprising the steps of
(a) iodination of compound of formula (III) with sodium iodide and sodium hypochlorite in the presence of an aliphatic amine to obtain Levothyroxine of formula (II)

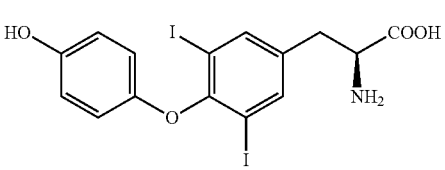

(III)

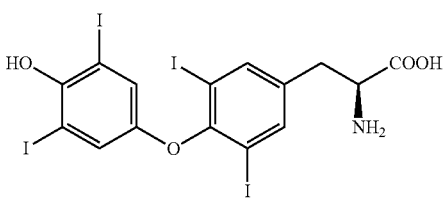

(II)

(b) treating Levothyroxine of formula (II) with sodium hydroxide to obtain Levothyroxine disodium of formula (IV)

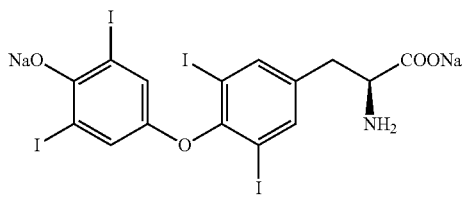

(IV)

(c) converting Levothyroxine disodium of formula (IV) to Levothyroxine sodium of formula (I)

The iodination reaction in step (a) is carried out in the presence of an aliphatic amine. The aliphatic amine is selected from the group consisting of methyl amine, ethyl amine, propyl amine, isopropyl amine, tert-butyl amine, diisopropyl amine, diisopropyl ethyl amine, n-hexyl amine, morpholine and triethylamine or mixtures thereof. In a preferred embodiment said aliphatic amine is selected from methyl amine, tert-butyl amine, diisopropyl amine and morpholine.

The iodination reaction in step (a) is carried out in a suitable solvent. As suitable solvent, water, dioxane, lower aliphatic alcohols such as methanol or ethanol or mixtures thereof may be used. In a preferred embodiment, iodination reaction is carried out in a water or methanol or mixtures thereof. Iodination reaction is conveniently carried out at a temperature of from 0° C. to 40° C., preferably at 20° C. to 30° C. The compound of formula (II) was isolating by methods known in the art.

In a preferred embodiment of step (b), Levothyroxine of formula (II) was treated with sodium hydroxide to obtain Levothyroxine disodium salt of formula (IV). This step is carried out optionally in a solvent. A suitable solvent is selected from the group consisting of water, alcohols, amides, sulphoxides, ethers, hydrocarbons, halogenated hydrocarbons, ketones, esters and nitriles or mixtures thereof. Examples of suitable solvent includes, but are not limited to water, methanol, ethanol, n-propanol, isopropanol, butanol, iso-butanol, ethyl acetate, methyl acetate, tertiary butyl acetate, isopropyl acetate, acetone, methyl isobutyl ketone, methyl ethyl ketone, diethyl ketone, dimethyl ketone, methyl isobutyl ketone, toluene, ethyl ether, methyl ether, diisopropylether, methyltertbutylether, dioxane, tetrahydrofuran, N,N-dimethylformamide, N-methyl acetamide, N,N-dimethylacetamide, dimethylsulfoxide, 1,1-dichloroethane, dichloromethane, chloroform, acetonitrile, benzene, xylene or mixtures thereof. This step (b) is carried out at a temperature of from 40° C. to 100° C., preferably at 80° C. to 90° C.

In a preferred embodiment, step (b) is carried out by reacting Levothyroxine of formula (II) with aqueous sodium hydroxide in alcoholic solvent such as n-propanol and isolating the compound of formula (IV) by methods known in the art.

In step (c), the Levothyroxine sodium salt of formula (I) may be obtained from corresponding Levothyroxine disodium salt of formula (IV) which consists in adding acidic solution followed by addition of sodium source such as sodium bicarbonate or sodium carbonate. This step is carried out optionally in a solvent. A suitable solvent is selected from the group consisting of water, alcohols, amides, sulphoxides, ethers, hydrocarbons, halogenated hydrocarbons, ketones, esters and nitriles or mixtures thereof. Examples of suitable solvent includes, but are not limited to water, methanol, ethanol, n-propanol, isopropanol, butanol, isobutanol, ethyl acetate, methyl acetate, tertiary butyl acetate, isopropyl acetate, acetone, methyl isobutyl ketone, methyl ethyl ketone, diethyl ketone, dimethyl ketone, methyl isobutyl ketone, toluene, ethyl ether, methyl ether, diisopropylether, methyltertbutylether, dioxane, tetrahydrofuran, N,N-dimethylformamide, N-methyl acetamide, N,N-dimethylacetamide, dimethylsulfoxide, 1,1-dichloroethane, dichloromethane, chloroform, acetonitrile, benzene, xylene or mixtures thereof.

In a preferred embodiment, Levothyroxine sodium salt of formula (I) is obtained by addition of acetic acid or HCl to a aqueous solution of Levothyroxine disodium salt of formula (IV) in suitable alcoholic solvent at a temperature 55-60° C. followed by adding aqueous solution of sodium source such as sodium bicarbonate or sodium carbonate keeping the temperature at 55-60° C. The reaction mixture was further heated to 80-90° C. followed by cooling at a temperature 5-10° C. to obtain Levothyroxine sodium salt of formula (I).

In a most preferred embodiment of the invention, the Levothyroxine sodium salt of formula (I) is obtained by addition of acetic acid in to the mixture of Levothyroxine disodium salt of formula (IV) in water and n-propanol followed by addition of aqueous solution of sodium carbonate and isolating the Levothyroxine sodium salt of formula (I) by methods known in the art.

The purity of Levothyroxine sodium obtained by the process of the present invention is greater than 99%, preferably greater than 99.8%. The process described in the present invention provides an increasing in the yields and purity comprising the use of sodium iodide and sodium hypochlorite as iodinating agent.

EXPERIMENTAL

Following Examples are set forth to aid in the understanding of the invention, and are not intended and should not be interpreted as a limitation thereon. Modifications to reaction conditions, for example, temperature, duration of the reaction or combinations thereof, are envisioned as part of the present invention. The compounds obtained by using the general reaction sequences may be of insufficient purity. These compounds can be purified by using any of the methods for purification of organic compounds known to persons skilled in the art, for example, crystallization using different solvents in suitable ratios. The starting material is commercially available or can be prepared according to methods known to one skilled in the art.

Example 1

Preparation of Levothyroxine Sodium

Step 1: Preparation Levothyroxine 3,5-Diiodo thyronine (50 gm, 0.095 moles) was added in methanolic methyl amine (250 mL) at 20-30° C. followed by addition sodium iodide (49.99 gm, 0.333 moles) and reaction mixture was stirred to get a clear solution. Aqueous solution of sodium hypochlorite [Preparation: sodium hypochlorite (464 mL, 0.333 moles) in water (193 mL)] was slowly added in the reaction mixture and mixture was stirred for 2-4 hr. After completion of the reaction, the mixture was cooled at 5-10° C. and acidified to pH 4.0-5.0 using 50% hydrochloric acid (~22 mL). The reaction mixture was stirred for 30 min at 25-30° C. The resultant solid was filtered and spray wash with methanol (50 mL). The obtained solid was dried at 50° C. under reduced pressure to get title compound (weight: 72 gm, yield 97%).

Step 2: Preparation Levothyroxine Sodium

Levothyroxine (50 gm, 0.064 moles) was dissolved in n-Propanol (250 mL) and mixture was stirred at 80-90° C. Aqueous sodium carbonate solution [preparation: Sodium carbonate (13.64 gm, 0.128 moles) in water (50 mL)] was added in to the reaction mixture to get a clear solution at 80-90° C. The reaction mixture was stirred for 1 hr. After completion of the reaction, the mixture was cooled at 0-5° C. and further stirred for 30 min at same temperature. The resultant solid was filtered and spray wash with n-propanol (50 mL). The obtained solid was dried at 50° C. under reduced pressure to get Levothyroxine Sodium (weight: 35 gm, yield 68%).

Example 2

Preparation of Levothyroxine Sodium

Step 1: Preparation of Levothyroxine

Aqueous methyl amine (25 ml) was added to the mixture of 3, 5 diiodo-L-thyronine (10 gm, 0.019 moles) and water (10 ml) at 20-30° C. Sodium iodide (8.57 gm, 0.57 moles) and sodium hypochlorite solution (3.54 gm, 0.47 moles) were added keeping the temperature at 20-30° C. and the reaction mixture was stirred for 2-4 hrs. The reaction mass was quenched with aqueous sodium thiosulfate solution (10% w/v, 20 ml) and pH was adjusted to 4.0-5.0 using dil HCl. The resultant slurry was filtered, washed with water (20 ml) and methanol (20 ml). The obtained solid was dried under vacuum to yield the title compound (weight: 13.6 gm, Yield: 92%).

Step 2: Preparation of Levothyroxine Disodium Salt

Aqueous sodium hydroxide solution (1.54 gm, 0.0386 moles in 10 ml water) was added to the mixture of Levothyroxine (10 gm, 0.0128 moles) and n-propanol (80 ml) and mixture was further charcolised (0.5 gm) at 80-90° C. The reaction mass was filtered, cooled to 60-65° C., further stirred followed by cooling to 25-30° C. The resultant slurry was filtered, washed with n-propanol (20 ml) followed by vacuum drying at 45-50° C. to afford Levothyroxine disodium salt (weight: 9.5 gm, Yield: 91%).

Step 3: Preparation of Levothyroxine Sodium

Levothyroxine disodium (10 gm, 0.0121 moles) was dissolved in mixture of n-propanol (35 ml) and water (25 ml). The reaction mixture was heated to 55-60° C. and filtered. Solution of acetic acid (2.19 gm, 0.0365 moles in 25 ml water) was added keeping the temperature at 55-60° C.

To this was added solution of aqueous sodium carbonate solution (3.86 gm, 0.0365 moles in 20 ml water) and mixture was heated to 80-90° C. The reaction mass was cooled to 5-10° C., filtered and washed with water (20 ml). The resultant solid was dried under vacuum at 30-35° C. till water content is 6.0% to 10% to afford Levothyroxine sodium (weight: 7.8 gm, Yield: 81%, purity: 99.8%).

Example 3

Preparation of Levothyroxine

Tert-butyl amine (6.9 gm, 0.095 moles) was added to the mixture of 3, 5 diiodo-L-thyronine (5 gm, 0.0095 moles) and sodium iodide (4.4 gm, 0.0285 moles) in methanol (25 ml) at 20-30° C. Sodium hypochlorite solution (46.5 ml, 0.02375 moles) was added to the mixture keeping the temperature at 20-30° C. and the reaction mixture was stirred for 2-4 hrs. The reaction mass was quenched with aqueous sodium sulphite solution (1 gm in 10 ml water) and pH was adjusted to 4.0-5.0 using 1:1 HCl. The reaction mixture was stirred and resultant slurry was filtered, washed with methanol (20 ml). The obtained solid was dried under vacuum to yield the title compound (weight: 7.4 gm, yield: 100%).

Example 4

Preparation of Levothyroxine

Cooled solution of Morpholine (2.2 ml, 0.0285 moles) and sodium hypochlorite solution was added to the mixture of 3, 5 diiodo-L-thyronine (5 gm, 0.0095 moles) and sodium iodide (4.3 gm, 0.0285 moles) in water (25 ml) at 20-30° C. The reaction mixture was stirred for 2-4 hrs. The reaction mass was quenched with aqueous sodium thiosulfate solution (5 gm in 10 ml water) and mixture was heated to 80-90° C. The reaction mass was cooled to 30° C. and to this was added solution of ammonium sulphate (5 gm in 10 water). The resultant mixture was filtered and washed with water (10 ml). The resultant solid was dried under vacuum drying at 30-35° C. to afford Levothyroxine (weight: 6.9 gm, yield: 93%)

Example 5

Preparation of Levothyroxine

Di-isopropyl amine (10 ml) was added to the mixture of 3, 5 diiodo-L-thyronine (10 gm, 0.019 moles) and sodium iodide (8.5 gm, 0.057 moles) in methanol (30 ml) at 20-30° C. Sodium hypochlorite solution (66 ml, 0.0475 moles) was added to the mixture keeping the temperature at 20-30° C. and the reaction mixture was stirred for overnight. The reaction mass was quenched with aqueous sodium sulphite solution (2 gm in 20 ml water) and pH was adjusted to 4.0-5.0 using 1:1 HCl. The reaction mixture was stirred and resultant slurry was filtered, washed with methanol (20 ml). The obtained solid was dried under vacuum to yield the title compound (weight: 14.3 gm, yield: 97%).

The invention claimed is:
1. A process for the preparation of Levothyroxine of formula (II)

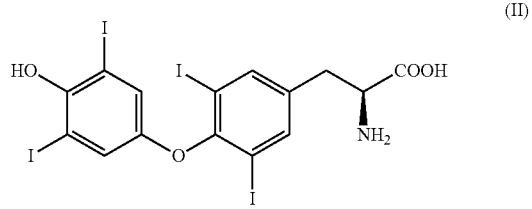

comprising iodination of compound of formula (III)

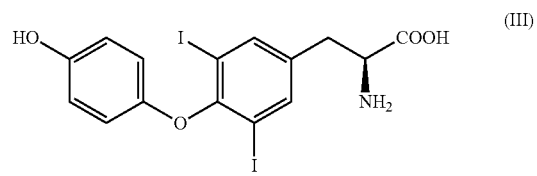 [SMILES: N[C@@H](Cc1cc(I)c(Oc2ccc(O)cc2)c(I)c1)C(=O)O]

with sodium iodide and sodium hypochlorite in the presence of an aliphatic amine.

2. The process according to claim 1, wherein said aliphatic amine is selected from the group consisting of methyl amine, ethyl amine, propyl amine, isopropyl amine, tert-butyl amine, diisopropyl amine, diisopropyl ethyl amine, n-hexyl amine, morpholine, triethylamine, and mixtures thereof.

3. The process according to claim 1, wherein said iodination reaction is carried out in suitable solvent comprising water, dioxane, methanol, ethanol, or mixtures thereof.

4. The process according to claim 1, further comprising reacting Levothyroxine of formula (II) with sodium carbonate or sodium bicarbonate optionally in a solvent to obtain Levothyroxine sodium of formula (I)

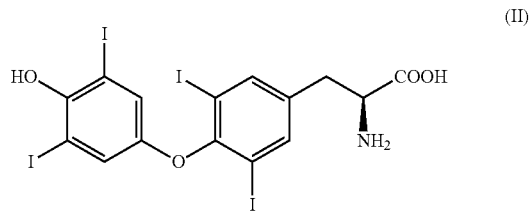

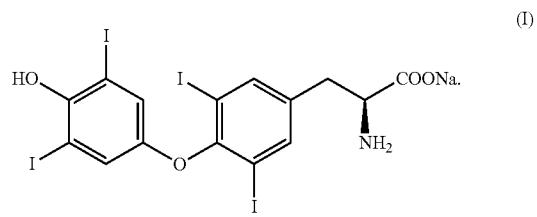

5. A process for the preparation of Levothyroxine sodium of formula (I)

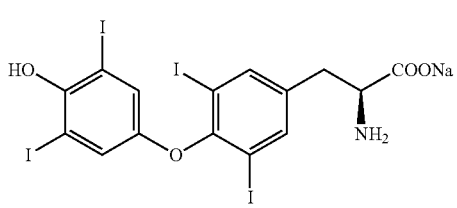
(I)

comprising the steps of
(a) iodination of compound of formula (III) with sodium iodide and sodium hypochlorite in the presence of an aliphatic amine to obtain Levothyroxine of formula (II)

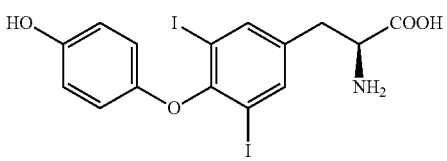
(III)

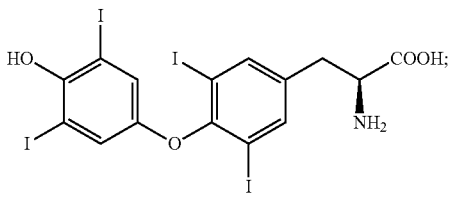
(II)

(b) treating Levothyroxine of formula (II) with sodium hydroxide to obtain Levothyroxine disodium of formula (IV)

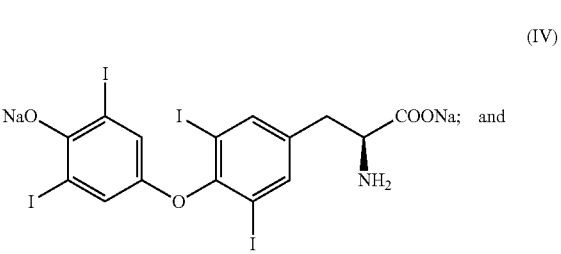
(IV)

(c) converting Levothyroxine disodium of formula (IV) to Levothyroxine sodium of formula (I).

6. The process according to claim 5, wherein said aliphatic amine is selected from the group consisting of methyl amine, ethyl amine, propyl amine, isopropyl amine, tert-butyl amine, diisopropyl amine, diisopropyl ethyl amine, n-hexyl amine, morpholine, triethylamine, and mixtures thereof.

7. The process according to claim 5, wherein said iodination reaction is carried out in suitable solvent comprising water, dioxane, methanol, ethanol, or mixtures thereof.

8. The process according to claim 5, wherein Levothyroxine sodium of formula (I) is obtained by adding acidic solution to the Levothyroxine disodium of formula (IV) followed by addition of sodium bicarbonate or sodium carbonate.

9. The process according to claim 8, wherein said acidic solution is acetic acid or hydrochloric acid (HCl).

10. The process according to claim 5, wherein step (b) and/or step (c) are carried out in a suitable solvent comprising water, methanol, ethanol, n-propanol, isopropanol, butanol, iso-butanol, or mixture thereof.

* * * * *